United States Patent
Ghanbari et al.

(10) Patent No.: US 10,525,044 B2
(45) Date of Patent: Jan. 7, 2020

(54) TREATMENT FOR CHEMOTHERAPY-INDUCED PERIPHERAL NEUROPATHY

(71) Applicant: Panacea Pharmacuetical Inc.

(72) Inventors: Hossein Ghanbari, Potomac, MD (US); Zhi-Gang Jiang, Gaithersburg, MD (US)

(*) Notice: Subject to any disclaimer, the term of this patent is extended or adjusted under 35 U.S.C. 154(b) by 0 days.

(21) Appl. No.: 15/828,726

(22) Filed: Dec. 1, 2017

(65) Prior Publication Data
US 2018/0200236 A1 Jul. 19, 2018

Related U.S. Application Data

(63) Continuation of application No. 15/015,559, filed on Feb. 4, 2016, and a continuation-in-part of application No. 13/848,262, filed on Mar. 21, 2013, now abandoned.

(51) Int. Cl.
| | |
|---|---|
| *A61K 31/44* | (2006.01) |
| *A61K 9/127* | (2006.01) |
| *A61K 9/08* | (2006.01) |
| *A61K 9/107* | (2006.01) |
| *A61P 25/02* | (2006.01) |
| *A61K 9/00* | (2006.01) |

(52) U.S. Cl.
CPC ............ *A61K 31/44* (2013.01); *A61K 9/0019* (2013.01); *A61K 9/08* (2013.01); *A61K 9/1075* (2013.01); *A61K 9/127* (2013.01); *A61P 25/02* (2018.01)

(58) Field of Classification Search
CPC ...................................................... A61P 25/02
See application file for complete search history.

(56) References Cited

U.S. PATENT DOCUMENTS

2006/0160826 A1* 7/2006 Ghanbari ........... A61K 31/4166
514/255.06
2012/0258180 A1* 10/2012 Giranda ............. A61K 31/4184
424/649

OTHER PUBLICATIONS

Chen et al., PAN-811 (3-Aminopyridine-2-carboxaldehyde thiosemicarbazone), a Noval Neuroprotectant, Elicits Its Function in Primary Neuronal Cultures by Up-regulating BCL-2 Expression, 2005, Neuroscience, vol. 135, pp. 191-201 (Year: 2005).*

* cited by examiner

*Primary Examiner* — Nannette Holloman
(74) *Attorney, Agent, or Firm* — John W. Ryan

(57) ABSTRACT

The present invention provides methods and compositions for treating chemotherapy induced peripheral neuropathy. One embodiment of the present invention is directed to a method of treating chemotherapy induced peripheral neuropathy by administering to a patient in need at least one thiosemicarbazone compound.

12 Claims, 5 Drawing Sheets

(b)

(c)

(a)

(b)

(c)

TREATMENT FOR CHEMOTHERAPY-INDUCED PERIPHERAL NEUROPATHY

BACKGROUND OF THE INVENTION

Chemotherapy-induced peripheral neuropathy (CIPN) is one of the most common, serious side effects that can lead to dose reductions or early discontinuation of chemotherapy, reducing the efficacy of cancer treatments. It can cause debilitating symptoms and also significantly impacts the patient's quality of life. An estimated 30 to 40 percent of cancer patients treated with chemotherapy experience CIPN.

The peripheral nervous system (PNS) consists of sensory neurons running from stimulus receptors that inform the central nervous system (CNS) of the stimuli, and motor neurons running from the spinal cord to the effectors that take action. In CIPN, an anticancer drug could impair both sensory and motor functions. The symptoms usually start in the hands and/or feet and creep up the arms and legs. Sometimes it feels like a tingling or numbness. Other times, it's more of a shooting and/or burning pain or sensitivity to temperature. It can include sharp, stabbing pain. CIPN can also lead to hearing loss, blurred vision and change in taste. CIPN can make it difficult to perform normal day-to-day tasks like buttoning a shirt, sorting coins in a purse, or walking. In addition, the motor neuron dysfunction manifest as cramps, difficulty with fine motor activities (e.g. writing or dialing a phone), gait disturbances, paralysis, spasms, tremors and weakness.

CIPN may result from the use of numerous chemotherapeutic agents, including, but limited to, Ixabepilone (Ixempra Kit), arsenic trioxide (Trisenox), cytarabine (Cytosar-U, Depocyt, generics), etoposide, hexamethylmelamine (altretamine [Hexalen]), Ifosfamide (Ifex, generics), methotrexate (Trexall, generics), procarbazine (Matulane) and vinblastine. The chemotherapeutic drugs that most commonly elicit CIPN include platinum compounds (cisplatin, carboplatin, oxaliplatin), vincristine, taxanes (docetaxel, paclitaxel), epothilones (ixabepilone), bortezomib (Velcade), thalidomide (Thalomid) and lenalidomide.

For treating the pain associated with CIPN, agents that appear promising include the antidepressants duloxetine and venlafaxine, which are both serotonin/norepinephrine-reuptake inhibitors. Another promising agent is a topical compound of the muscle-relaxant baclofen, the antidepressant amitriptyline, and the analgesic ketamine Outside of clinical trials, CIPN symptoms are commonly managed in a manner similar to other types of nerve pain—that is, with a combination of physical therapy, complementary therapies such as massage and acupuncture, and medications that can include steroids, antidepressants, anti-epileptic drugs, and opioids for severe pain. But these therapies have not demonstrated true efficacy for CIPN, and virtually all of the drugs to treat peripheral neuropathy carry side effects of their own.

The actual causes of CIPN, on the cellular and tissue level, is still largely a matter of speculation. Oxidative stress may play a key role in CIPN. It was found that antioxidant machinery (e.g. plasma glutathione (GSH) and $\alpha$- and $\gamma$-tocopherol concentrations) of cancer patents with chemotherapy decreased and the GSH redox state became more oxidized. In a rat model of painful oxaliplatin-induced neuropathy, oxidative stress was found to be an important component that mediates pain. In the plasma of oxaliplatin-treated rats, the increases of carbonylated protein and thiobarbituric acid reactive substances in the sciatic nerve and the spinal cord indicated the resultant protein oxidation and lipoperoxidation in these locations, respectively. Oxidative imbalance manifests itself as a mediator of inflammatory pain as well. Use of the anticancer drug cisplatin results in severe cell death of sensory neurons derived from dorsal root ganglia following increase in oxidative stress. Oxidative stress is also found to impair the autonomic nervous system and manifests itself in symptoms such as hearing loss. The results from antioxidants also support a key role of oxidative stress in mediating CIPN. The antineuropathic effect of antioxidant silibinin or $\alpha$-tocopherol shows as about 50% oxaliplatin-induced behavioral alterations. Administration of anticancer drug bortezomib or oxaliplatin, which elicits TRPA1-dependent hypersensitivity, produced a rapid, transient increase in plasma of carboxy-methyllysine, a by-product of oxidative stress. Short-term systemic treatment with either HC-030031 or $\alpha$-lipoic acid (an antioxidant) could completely prevent hypersensitivity if administered before the cytotoxic drug. The findings highlight a key role for early activation/sensitization of TRPA1 by oxidative stress by-products in producing CIPN. For preventing the onset of CIPN, further clinical testing of many antioxidative stress agents, such as glutathione, acetyl-L-carnitine and alpha-lipoic acid has been suggested.

Another mechanism underlying CIPN is excitotoxicity where increased release of glutamate forces N-methyl D-aspartate (NMDA) receptors to remain open, allowing increased calcium flux into neurons, resulting in overexcitation and eventually neuronal rupture. The end result of this process is pain without a painful stimulus, also known as neuropathic pain. N-Acetyl-aspartyl-glutamate (NAAG) is an abundant neuropeptide widely distributed in the central and peripheral nervous system which is physiologically hydrolyzed by the enzyme glutamate carboxypeptidase into N-Acetyl-aspartyl (NAA) and glutamate. Glutamate carboxypeptidase inhibition could reduce the severity of chemotherapy-induced peripheral neurotoxicity in rat.

As there are no proven treatments, there is a need for methods to properly treat chemotherapy-induced peripheral neuropathy. The present invention provides just such a method.

SUMMARY OF THE INVENTION

The present invention is directed to a method of treating chemotherapy-induced peripheral neuropathy.

One embodiment of the present invention is directed to a method of treating chemotherapy-induced peripheral neuropathy by administering to a patient in need at least one thiosemicarbazone compound.

Another embodiment of the present invention is directed to a method of treating chemotherapy-induced peripheral neuropathy by administering to a patient in need a composition comprising 3-aminopyridine-2-carboxaldehyde thiosemicarbazone, or an analogue thereof.

Another embodiment of the present invention is directed to a method of treating chemotherapy-induced peripheral neuropathy by administering to a patient in need a composition comprising 3-aminopyridine-2-carboxaldehyde thiosemicarbazone the step of administering is intravenous, intraperitoneal, subcutaneous, intramuscular, topical, transdermal or oral.

The present invention further encompasses methods of treating chemotherapy-induced peripheral neuropathy by administering a composition comprising a compound of Formula I, or an analogue thereof:

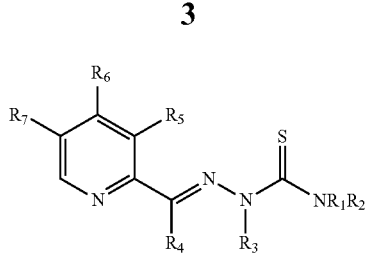

Wherein R, $R_1$, $R_2$, $R_3$, and R are independently selected from the group consisting of hydrogen, C1-8alkyl, C2-8alkenyl, C2-8alkynyl, C3-8cycloalkyl, C1-8haloalkyl, C6-10aryl, amino-C1-8alkyl, hydroxy-C1-8alkyl, C1-8alkoxye-C1-8alkyl, and C1-8alkanoyl, or $NR_1R_2$ taken in combination form a 3 to 7 member ring which may comprise 0, 1, or 2 additional ring heteroatoms selected from N, O, and S; $R_6$ is hydrogen, hydroxy, amino, or C1-8alkyl; $R_5$ and $R_7$ are independently selected from the group consisting of hydrogen, halide, hydroxy, thiol, amino, hydroxyamino, mono-C1-8alkylamino, di(C1-8alkyl)amino, C1-8alkoxy, C1-8alkyl, C1-8alkenyl, and C2-8alkynyl.

The present invention further encompasses methods of treating chemotherapy-induced neuropathy by administering a composition comprising a compound of Formula II, or an analogue thereof:

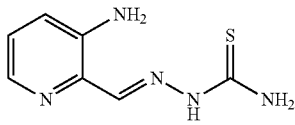

Figure symbols are *, $P<0.05$, compared with insult group alone (without PAN-811 treatment) by Student's t-test (one tail) and one-factor ANOVA followed by Tukey HSD test; #, $P<0.05$; ##, $P<0.01$, compared with noninsult/untreated control group by one-factor ANOVA followed with Tukey HSD test.

Figure 4:
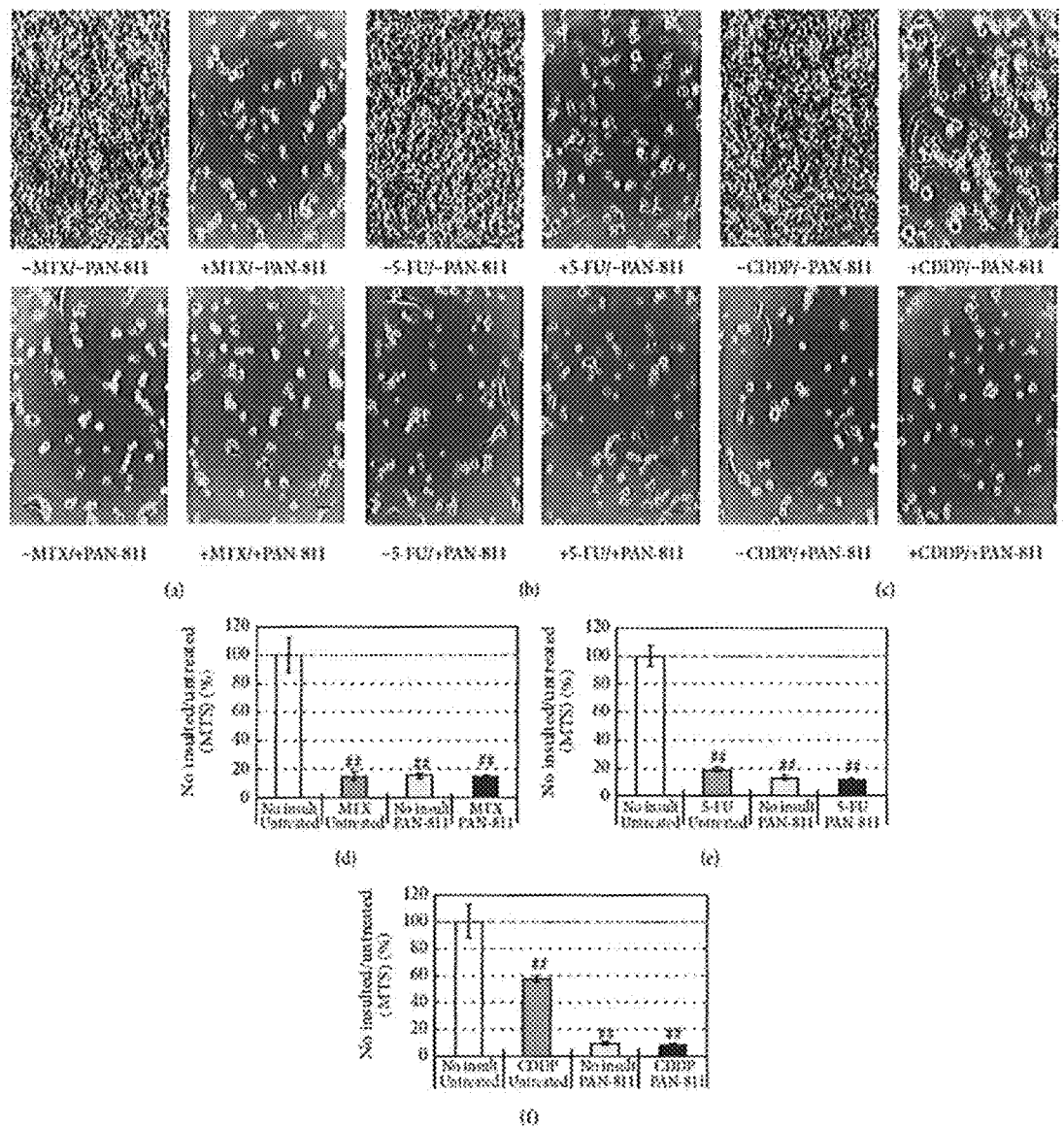

FIG. 4: No interference of PAN-811.Cl.$H_2$O with anticancer drug-induced cytotoxicity to mouse cancer cell line BNLT3. (a)-(c) Phase contrast photographs for BNLT3 cells that were treated without or with 10 μM PAN-811.Cl.$H_2$O and insulted with 100 μM MTX, 25 μM 5-FU, and 3.5 μM CDDP for 3 days, respectively (bar=50 μm). (d)-(f) MTX analysis corresponding to (a)-(c) (n=6). Data are expressed as % of noninsulted/untreated control. Figure symbol is ##, $P<0.01$, compared with noninsult/untreated control group by one-factor ANOVA followed with Tukey HSD test.

Figure 5:
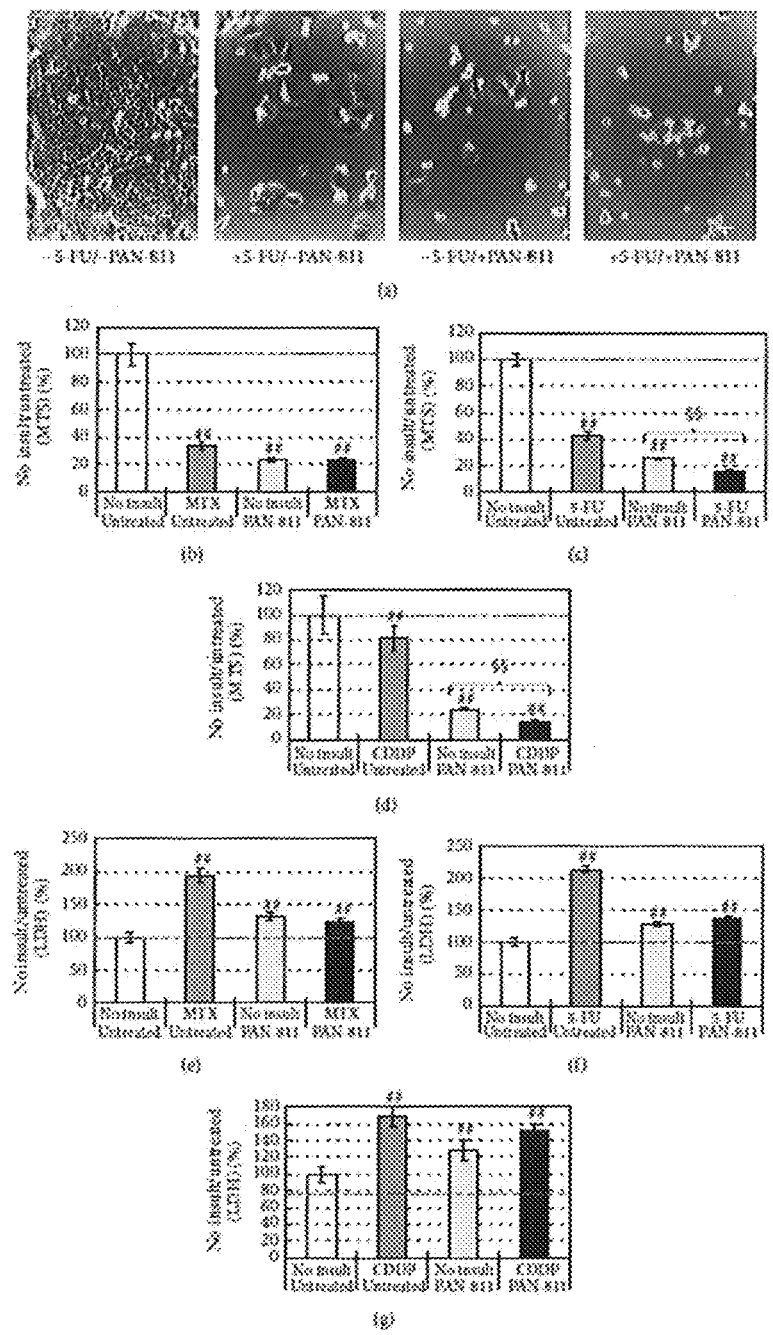

FIG. 5: Effects of PAN-811.Cl.$H_2$O on anticancer drug-induced cytotoxicities to human cancer cell H460. (a) Phase contrast photographs for the H460 cells that received 25 μM 5-FU, 10 μM PAN-811, or both for 3 days (bar=50 μm). (b)-(d) MTS analysis for the H460 cells that received 10 μM PAN-811.Cl.H2O, one of 100 μM MTX, 25 μM 5-FU, and 3.5 μM CDDP, or both 10 μM PAN-811.Cl.$H_2$O and one of these anticancer drugs for 3 days, respectively (n=6). (e)-(g) LDH analysis for (b)-(d) (n=6). Data are expressed as % of noninsulted/untreated control. Figure symbol is ##, $P<0.01$, compared with noninsult/untreated control group by one-factor ANOVA followed with Tukey HSD test.

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. Before explaining the disclosed embodiments of the present invention in detail, it is to be understood that the invention is not limited in its application to the details of any particular arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

The present invention is directed to a method for the treatment of chemotherapy induced peripheral neuropathy comprising the step of administering to a patient a composition comprising a thiosemicarbazone compound. The means for synthesis of thiosemicarbazone compounds useful in the methods of the invention are well known in the art. Such synthetic schemes are described in U.S. Pat. Nos.

5,281,715; 5,767,134; 4,447,427; 5,869,676 and 5,721,259; all of which are incorporated herein by reference in their entirety.

The chemical structures of PAN-811's analogues are shown in U.S. Pat. No. 7,456,179, and patent applications of 20090275587, 20060194810 and 20060160826 each of which are hereby incorporated by reference.

The pharmaceutical compositions required by the present invention typically comprise a compound useful in the methods of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer. The active compounds can be prepared with carriers that will protect the compound against rapid release, such as a controlled release formulation, including implants and microencapsulated delivery, systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes. Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., one or more thiosemicarbazones) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A compound of the invention can be formulated into a pharmaceutical composition wherein the compound is the only active agent therein. Alternatively, the pharmaceutical composition can contain additional active agents. For example, two or more compounds of the invention may be used in combination.

3-aminopyridine-2-carboxaldehyde thiosemicarbazone (hereinafter "PAN-811"), with a molecular weight of 195.24 Da, has demonstrated potent neuroprotective activities in several neurodegenerative models. PAN-811 was originally developed for cancer therapy due to its ability to inhibit ribonucleotide reductase, a key enzyme required for DNA synthesis. Our previous studies demonstrated that PAN-811 at concentration of 0.45 µM fully blocked ischemic neurodegeneration and at 1.2 µM completely halted hypoxia-induced neuronal cell death. PAN-811 was administered intracerebroventricularly (i. c. v.) at a dose of 50 µg per rat at 1 h after arterial occlusion. Staining of consecutive brain sections and computer-assisted quantitative analysis demonstrated that PAN-811 reduced the infarct volume by 59% in PAN-811 treated rats. We also investigated the effect of a single intravenous (i. v.) bolus injection of PAN-811. Two-hour middle cerebral artery occlusion (MCAo) with cerebral blood flow reduction of 75% or greater resulted in infarct formation, brain edema and a significant number of premature deaths. PAN-811 treatment reduced infarct volume in a dose dependent manner with a maximal protection of 50% at a dose of 2 mg/kg. PAN-811 treatment (2 mg/kg) also resulted in a 70% reduction in brain edema volume. Accordingly, the mortality in PAN-811 treated groups was collectively reduced by 44% (Jiang et al., 2008). Mechanistically PAN-811 prevents glutamate-induced excitatory cytotoxicity, veratridine-induced sodium channel opening that is related to $Ca^{2+}$ influx and staurosporine-induced apoptosis. Nearly complete neuroprotection against glutamate insult is observed in cultured neuronal cells if the cells were pre-treated with 10 µM PAN-811 for 24 h. In culture, ischemic condition results in a 19-fold increase in intracellular free calcium. PAN-811 at a dose of 5 µM reduced this elevated level by 72%. In a cell-free system by taking EDTA as a positive control, PAN-811 chelates free calcium as efficiently as EDTA. In addition, PAN-811 effectively suppresses oxidative stress in many ways. PAN-811 at a concentration as low as 1 µM suppressed in vitro hydrogen peroxide-induced LDH release by 78% (with P<0.01, compared to untreated/$H_2O_2$-insulted group) and at a concentration of 10 µM achieved maximal protection (by 90% comparing with untreated and $H_2O_2$-insulted group) with an $EC_{50}$ of ~0.55 µM. PAN-811 also inhibited oxidative stress-induced cell death of human Alzheimer's disease-derived and age-matched olfactory neuroepithelial cells via suppression of intracellular reactive oxygen species. Importantly, PAN-811 manifested as a free radical scavenger in a cell free system where PAN-811 reduced 500 µM of a stable free radical diphenylpicrylhydrazyl by 70%. Taken together, PAN-811 has manifested as a potent neuroprotectant with dual drug targets—oxidative stress and free calcium.

Based on the key roles of excitoneurotoxicity and oxidative stress in chemotherapy-induced peripheral neuropathy and also the potent free calcium chelating and antioxidative effects of PAN-811, we have discovered that PAN-811 is a therapeutic agent for chemotherapy-induced peripheral neuropathy. PAN-811 should inhibit chemotherapy-induced peripheral neuropathy that is not only caused with antimetabolites (cytarabine, gludarabine, fluorouracil, mercaptopurine, methotrexate, thioguanine, gemcitabine, hydroxyurea), mitotic inhibitors (vincristine, vinblastine, vinorelbine), topoisomerase inhibitors (topotecan, irenotecan), paclitaxel, docetaxel and asparaginase, but also with alkylating agents (busulfan, carmustine, lomustine, chlorambucil, cyclophosphamide, cisplatin, carboplatin, oxaliplatin, ifosamide, mechlorethamine, melphalan, thiotepa, dacarbazine, procarbazine), antitumor antibiotics (bleomycin, dactinomycin, daunorubicin, doxorubicin, idarubicin, mitomycin, mitoxantrone, plicamycin), topoisomerase II inhibitor (etoposide, teniposide), and radiation therapy. In addition, PAN-811 should inhibit chemotherapy-induced peripheral neuropathy caused by other anticancer drug, such as ixabepilone, arsenic trioxide, etoposide, hexamethylmelamine, ifosfamide, methotrexate, procarbazine, epothilones, bortezomib, thalidomide and lenalidomide.

Example 1

Materials and Methods

Neuronal Cell Culture. Mixed cortical and striatal neurons fromembryonic day 17 male Sprague-Dawley rats (tissue obtained from NIH) were seeded into poly-D-lysine coated 96-well plates at density of 50,000 cells/well and initially cultured at 37° C., 5% CO2, in neurobasal medium (NB) with B27 supplement (Invitrogen) containing full strength of AOs to obtain highly enriched (95%) neurons. Since AOs, including vitamin E, vitamin E acetate, superoxide dismutase (SOD), catalase (CAT), and GSH, are additives to culture medium, reduction of AO concentration in culture medium provides an approach to determine the level of OS involvement in a neurotoxic process. In our study, the culture medium was replaced at a 50% ratio with NB plus B27 minus AOs twice at days 7 and 9 to set AO concentrations as 50% and 25%, respectively. At 16 days in vitro (d.i.v.), a fraction of the culture medium was harvested for lactate dehydrogenase (LDH) assay, and then AO concentration was reduced to 12.5% and cultured for a further 5 hours prior to ending the experiment.

Cancer Cell Culture. The mouse liver cancer cell line BNLT3 (gift of Dr. Jack Wands, Brown University) and the human lung cancer cell line H460 (ATCC) were seeded into 96-well plates at a density of 4,000 cells/well and cultured at 37° C., 5% CO2, in DMEM (11965, Gibco) supplemented with 10% fetal bovine serum, 20 mM HEPES, 1 mM sodium pyruvate, and 24 ng/mL gentamycin (all reagents came from Gibco).

Cell Insults and Treatments. Determination of concentration for each anticancer drug in our experiments was based on its reported concentration in human cerebral spinal fluid (CSF) in chemotherapy, literature report of its neurotoxicity in culture, and our preliminary in vitro experimental data. At 13 d.i.v., the neuronal cell cultures were insulted with 100 µM of MTX (M9929, Sigma), 25 µM of 5-FU (F6627, Sigma), or 3.5 µM of CDDP (sc-200896, Santa Cruz) for 3 days in absence or presence of PAN 811.Cl.H2O. For ROS examination, the neurons were insulted with both 100 µM of MTX and 25 µM of 5-FU by 15 d.i.v. PAN-811.Cl.H2O was added to cultures to final concentrations of 1.25, 2.5, 5, and 10 µM at the same time as addition of the anticancer drugs. For cancer cell lines, the cells were insulted by the second day of cell seeding with the same concentration of MTX, 5-FU, or CDDP as used in neuronal culture in the absence or presence of 10 µM PAN-811.Cl.H2O for another 3 days.

Quantitative Assays and Morphological Assessment. Cell membrane integrity and mitochondrial function of either neurons or cancer cells were measured with LDH and 3-(4,5-dimethylthiazol-2-yl)-5-(3-carboxymethoxyphenyl)-2-(4-sulfophenyl)-2H-tetrazolium [MTS] analyses, respectively. The latter has been used to quantify cell survival. For the LDH assay, a mixture of a 35 µL aliquot of culture supernatant and 17.5 µL of Mixed Substrate, Enzyme and Dye Solutions (Sigma) was incubated at room temperature (RT) for 30 minutes. For the MTS assay, 10 μL of MTS reagent (Promega) was added to a culture well containing neurons in 50 μL of medium. The preparations were incubated at 37° C. for 2 hours. The preparations for both assays were then spectrophotometrically measured at 490 nm using a 96-well plate reader (Mode 550, Bio-Rad). Neuronal cell death was morphologically determined based on the integrity of the cell soma and continuity of neuronal processes. The change in number of cancer cells was judged directly by cell density. Cells were photographed under an inverted phase contrast microscope (IX 70, Olympus) using 10× or 20× objective.

ROS Examination. Neurons were incubated in 15 μM dihydrorhodamine 123 (DHR 123, Molecular Probes) for 30 min at 37° C. to determine intramitochondrial ROS levels. Fluorescence was photographed by using a fluorescentmicroscope and quantified by excitation at 485 nm and emission at 520 nm using a 96-well plate reader (Model 550, Bio-Rad).

Data Analysis. Data were generated from 4-6 replicate wells, expressed as mean±standard deviation (SD), and statistically evaluated at a significance level of 1% with one factor ANOVA or Student's t-test by using software VASSARSTATS (http://vassarstats.net/) followed by the Tukey HSD test. Figure symbols are as follows: #, $P<0.05$, and ##, $P<0.01$, compared with control; *, $P<0.05$, and **, $P<0.01$, compared with the insulted group; §§, $P<0.01$, compared with PAN-811 treated group by Student's t-test.

Results

Figure 1:
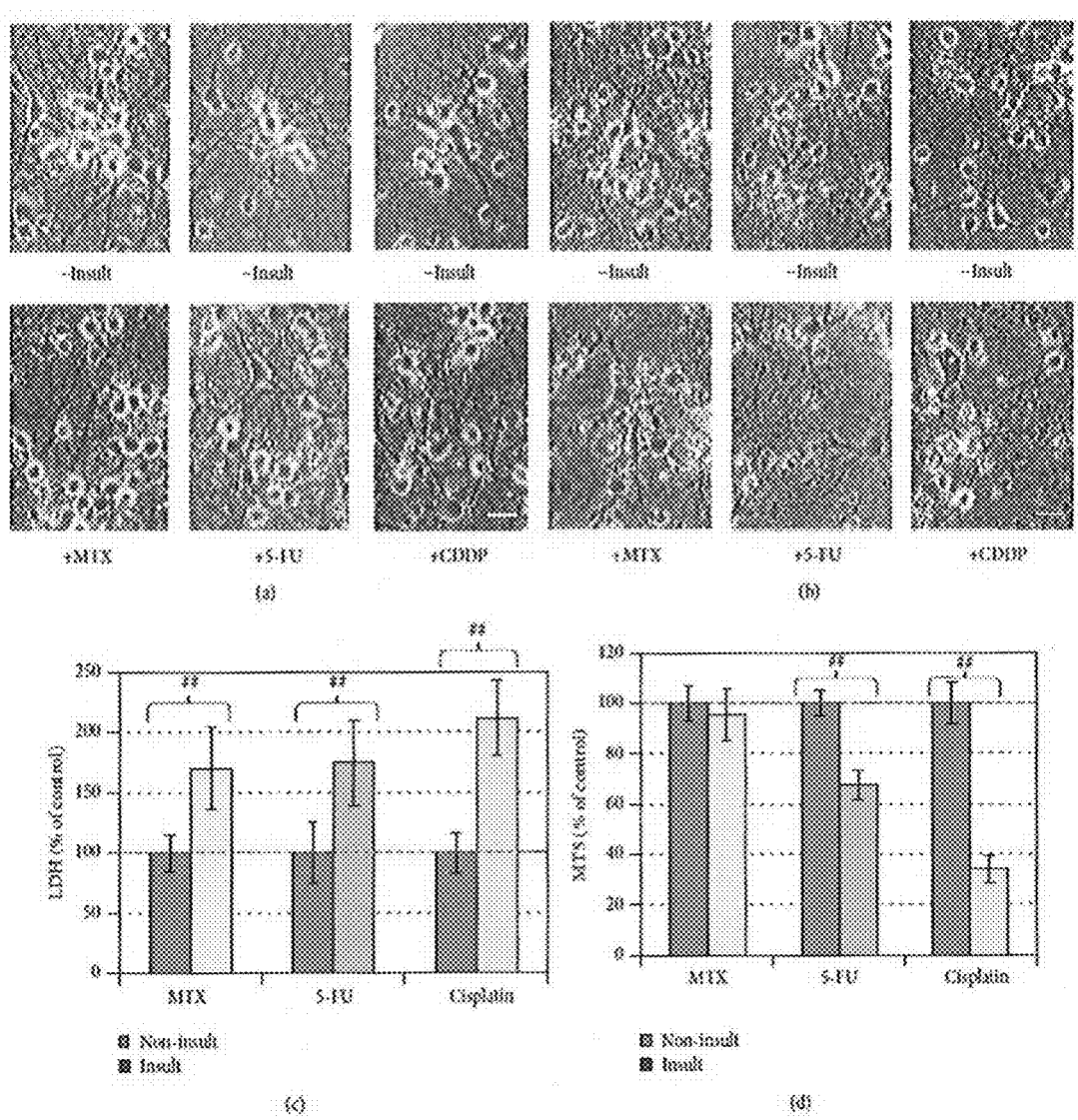
FIG. 1: Neurotoxicity of MTX, 5-FU, or CDDP in an AO-dependent manner. (a, b) Phase contrast photographs for neurons in 25% AO and 12.5% AO, respectively (bar=25 μm). (c) Cell membrane leakage was determined via the LDH analysis at the end of experiment for neurons in 25% AO (n=5). (d) Cell viability was determined with MTS analysis for neurons in 12.5% AO (n=5). The bar in green and bars in other colors indicate the cultures without an insult and with anticancer drug insults, respectively. LDH and MTS data are expressed as % of noninsulted control. Figure symbol is ##, $P<0.01$, compared with noninsult control group by Student's t-test.

MTX, 5-FU, or CDDP Elicited Neurotoxicity in an AOs-Dependent Manner. By 3 days following the insults, neither MTX at 100 μM, 5-FU at 25 μM, nor CDDP at 3.5 μM caused morphological changes, LDH release, or MTS reduction when neurons were cultured in the medium containing 100% or 50% AOs (data not shown). However, MTX, 5-FU, or CDDP at the same concentrations elicited significant LDH increase (indicating cell membrane leakage, FIG. 1(c)) in the culture supernatant when the AO concentration was reduced to 25%, although no cell damage was visible (FIG. 1(a)), and no change in MTS level was detectable (data not shown) under these conditions. When the AO concentration was reduced to 12.5% for 5 hours at 16 d.i.v., extensive neuronal cell death occurred in the cultures insulted with 25 μM 5-FU or 3.5 μM CDDP, as indicated by loss of cell bodies, together with interruption of neurite networks on the background (FIG. 1(b)). Corresponding to the morphological cell death, the MTS readings for 5-FU- and CDDP-insulted groups were reduced by 27% and 66%, respectively (FIG. 1(d)). MTX at 100 μM did not elicit significant MTS reduction (FIG. 1(d)) under 12.5% AO condition. Thus, the neurotoxicities elicited with MTX, 5-FU, or CDDP were dependent on AO reduction.

Figure 2:
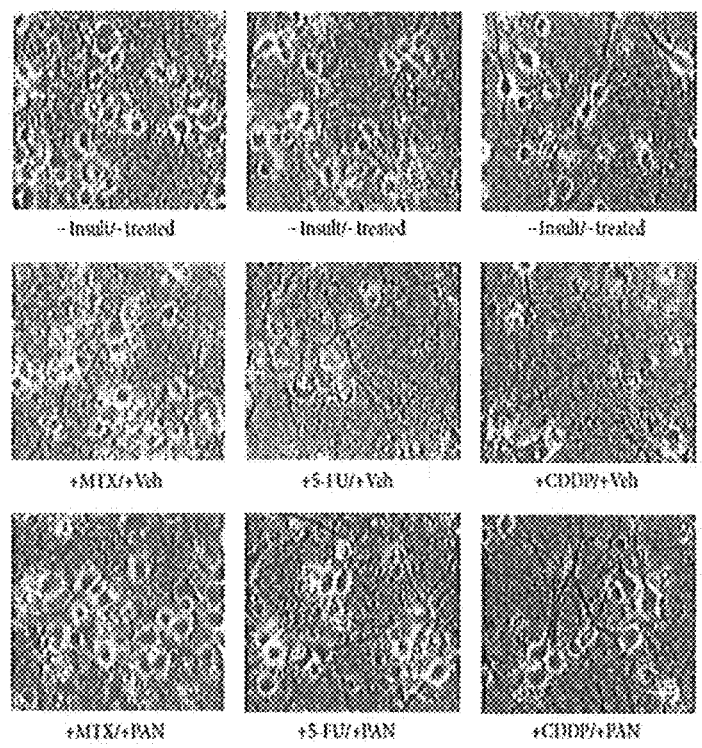
FIG. 2: Dose-dependent neuroprotection of PAN-811.Cl.$H_2$O against anticancer drug-induced neurotoxicity. (a) Phase contrast photographs for neurons in 12.5% AO (bar=25 μm; PAN: PAN-811·Cl.$H_2$O). (b) LDH analysis for (a) (n=5). (c) MTS analysis for (a) (n=6). The bar in green and bars in other colors in the graphs indicate the cultures without an insult and with anticancer drug insults, respectively. Data are expressed as % of noninsulted control. Figure symbols are *, $P<0.05$, and **, $P<0.01$, compared with insult group alone (without PAN-811 treatment) by one-factor ANOVA followed with Tukey HSD test.
Figure 2:
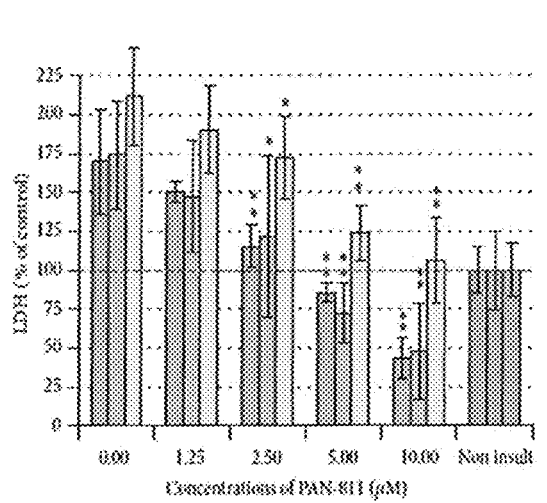
Figure 2:
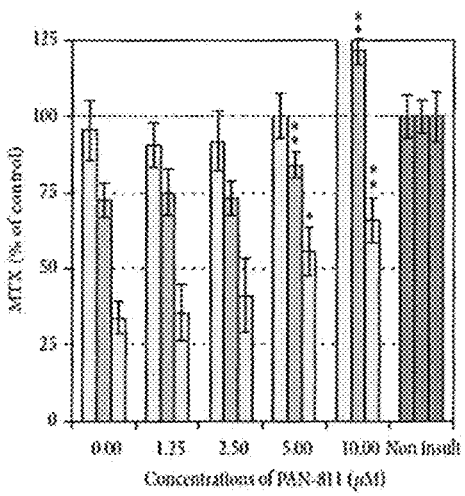

PAN-811 Dose-Dependently Suppresses MTX-, 5-FU-, or CDDP-Induced Neurotoxicity. We then examined PAN-811 for its effect on the anticancer drug-induced neurotoxicity at the 12.5% AO condition. MTX at 100 μM did not result in significant loss of cell number, while 5-FU at 25 μM or CDDP at 3.5 μM caused robust loss of neurons in culture (FIG. 2(a)). Correspondingly, MTX insult did not significantly affect the MTS reading, while 5-FU- and CDDP insulted cultures showed significant reduction in MTS readings (FIG. 2(c)). PAN-811 dose-dependently inhibited 5-FU- or CDDP-induced MTS reduction. PAN-811 at 10 μM completely blocked 5-FU-induced MTS reduction and inhibited CDDP-induced MTS reduction by 48%. The LDH release assay demonstrated that each of MTX at 100 μM, 5-FU at 25 μM, and CDDP at 3.5 μM resulted in significant increases in LDH reading (FIG. 2(b)). PAN-811 dose-dependently suppressed LDH increase caused by each anticancer drug. PAN-811 at 5 μM fully blocked LDH release in MTX-, 5-FU-, or CDDP-insulted cultures (with no statistically significant difference from untreated control culture by ANOVA analysis). Thus, PAN-81 was demonstrated as a potential neuroprotective compound for anticancer drug MTX-, 5-FU-, or CDDP-induced neurotoxicity.

Figure 3:
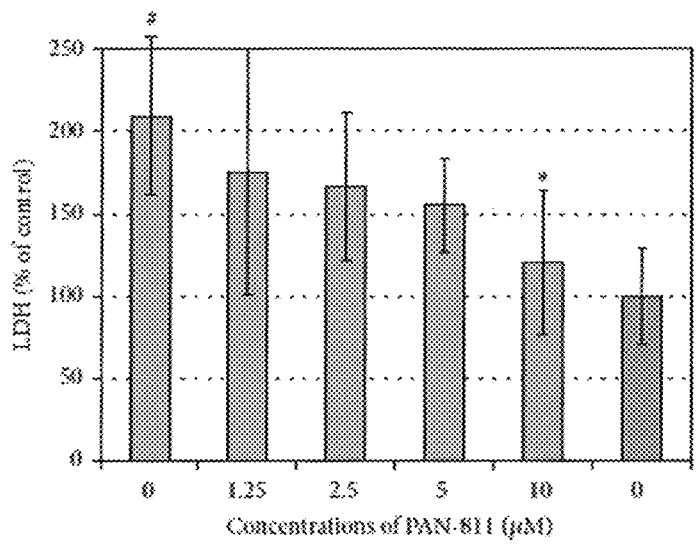
FIG. 3: Suppression of 5-FU/MTX-induced increases in LDH and DHR123 readings by PAN-811. (a) LDH release analysis for neurons that were cultured in 17.5% AOs containing medium and insulted with both 100 μM MTX and 25 μM 5-FU in the absence or presence of PAN-811.Cl.$H_2$O at different concentrations for 1 day (n=6). (b) Fluorescent microscope for neurons in 17.5% AOs-containing medium insulted with both 100 μM MTX and 25 μM 5-FU in the absence or presence of 10 μM PAN-811-Cl.$H_2$O for 1 day and incubated with DHR123 for 30 min (bar=50 μm). (c) Quantification of (b) at excitation at 485 nm and emission at 520 nm (n=4). Data are expressed as % suppression=[(Insulted&Untreated−Insulted&Treated)/(Insulted&Untreated−NonInsulted&Untreated)*100%].
Figure 3:
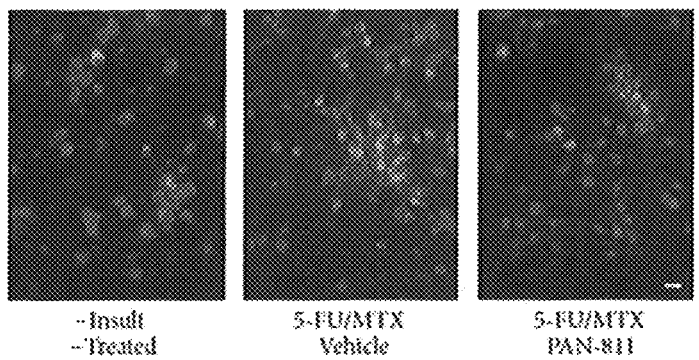
Figure 3:
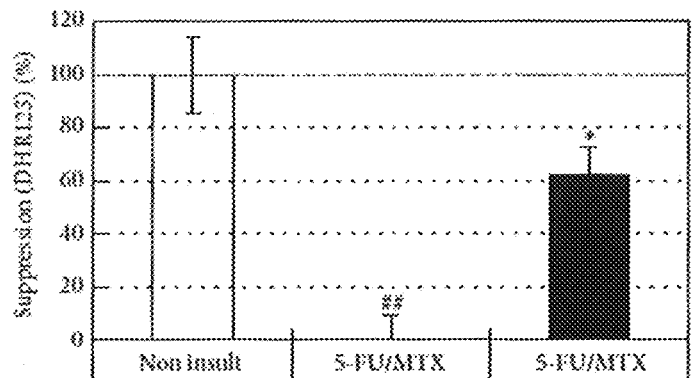

PAN-811 Suppresses Cell Membrane Leakage When MTX and 5-FU Are Coadministered. Since MTX and 5-FU are coadministered for cancer therapies in many cases, we were interested to know if PAN-811 can block neurotoxicity that is elicited with a combined insult with both MTX and 5-FU. An insult with a combined 100 μM MTX and 25 μM 5-FU resulted in a 109% increase in LDH reading by comparison with noninsulted control group ($P<0.05$ by ANOVA; FIG. 3(a)). PAN-811 showed concentration-dependent suppression of LDH release within the tested range from 1.25 to 10 μM. PAN-811 at 10 μM fully inhibited MTX/5-FU-elicited LDH increase.

PAN-811 Inhibits MTX- and 5-FU-Elicited OS. To understand the underlying mechanism for MTX- and 5-Fu induced neurotoxicity, a cell-permeable fluorogenic probe DHR 123 was used for the detection of intramitochondrial ROS. Neuronal insult with coadministered 100 μM MTX and 25 μM 5-FU greatly increased intensity of DHR 124 fluorescence (FIG. 3(b)), resulting in a 33.4% increase in DHR123 level in comparison with noninsulted group ($P<0.05$ by t-test, data not shown). PAN-811 at 10 μM provided significant suppression to the increased ROS, showing a 62.3% suppression rate (FIG. 3(c)).

PAN-811 Shows No Antagonistic Effect on MTX-, 5-FU-, or CDDP-Induced Cytotoxicity in BNLT3 Cells. To understand whether PAN-811 could interfere with anticancer efficacy of tested anticancer drugs, the mouse liver cancer cell line BNLT3 was cotreated with each anticancer drug at the concentrations used for elicitation of neurotoxicity and 10 μM PAN-811, the highest concentration used for neuronal protection in these experiments. A 3-day insult with 100 μM MTX severely reduced the cancer cell number (FIG. 4(a)). In the culture treated with 10 μM PAN-811 alone or cotreated with 100 μM MTX and 10 μM PAN-811, cell density was also much lower than that in no-insult control. Quantitatively, MTX at 100 μM reduced MTS reading by 85% (FIG. 4(d)), while PAN-811 at 10 μM reduced MTS reading to the same level as MTX. A cotreatment with both did not cause any further reduction in MTS reading when comparing with MTX alone. Similarly, 5-FU at 25 μM significantly reduced the cell density of the cancer cells, and a cotreatment with both 25 μM 5-FU and 10 μM PAN-811 significantly decreased the cell number as well (FIG. 4(b)). Quantitatively, 5-FU at 25 μM reduced MTS reading by 84%, which was less efficient than 10 μM PAN-811 group (FIG. 4(e)). A cotreatment with both caused a further reduction in MTS reading when comparing with 5-FU alone. No synergistic effect between 5-FU and PAN-811 could be detected. An insult with 3.5 μM CDDP also caused a decrease in the cell density (FIG. 4(c)), while a treatment with PAN-811 alone or a cotreatment with both 3.5 μM CDDP and 10 μM PAN-811 introduced a significant reduction in the cell density. Quantitatively, 3.5 μM CDDP reduced MTS reading by 44%, while 10 μM PAN-811 caused a 94% reduction in MTS reading (FIG. 4(f)). A cotreatment with both did not introduce an extra reduction in MTS reading by comparing with PAN-811 alone, despite showing much lower reading than CDDP alone ($P<0.01$). In general, PAN-811 did not show any inhibition in the effect of MTX, 5-FU, or CDDP on BNLT3 cells, neither did it demonstrate any synergistic effect with each tested anticancer drug on BNLT3 cell growth.

PAN-811 Shows No Antagonistic Effect on MTX-, 5-FU-, or CDDP-Induced Cell Death of H460 Cells, While Demonstrating a Synergistic Effect with 5-FU or CDDP on Suppression of the Cell Growth. To understand whether there is any negative effect of PAN-811 on the efficacy of tested anticancer drugs in humans, the human lung cancer cell line H460 was treated with each of these anticancer drugs at the concentrations used for elicitation of neurotoxicity, in the absence or presence of 10 µM PAN-811. A 3-day insult with 100 µM MTX, 10 µM PAN-811, or both robustly decreased the cell density of H460 in culture (data not shown). Quantitatively, 100 µM MTX and 10 µM PAN-811 reduced MTS readings by 67% and 76%, respectively. The MTS reading for a cotreatment with both 100 µM MTX and 10 µM PAN-811 was about the same as 10 µM PAN-811 alone (FIG. 5(b)). In membrane integrity analysis (FIG. 5(e)), 100 µM MTX resulted in a 95% increase in LDH reading in the culture supernatant, while 10 µM PAN-811 led to a 31% increase in the LDH reading. A cotreatment with 100 µM MTX and 10 µM PAN-811 reduced LDH reading by 70% when compared with MTX group (P<0.01 by ANOVA), indicating an inhibitory effect of PAN-811 on MTX-caused membrane leakage. Similarly, a 3-day treatment with 25 µM 5-FU, 10 µM PAN-811, or both robustly decreased the cell density of H460 in culture (FIG. 5(a)). Quantitatively, 25 µM 5-FU and 10 µM PAN-811 reduced MTS readings by 57% and 74%, respectively (FIG. 5(c)). In contrast, a cotreatment with 25 µM 5-FU and 10 µM PAN-811 reduced MTS readings by 84%, which shows a statistically significant difference from 5-FU (P<0.01) or PAN-811 alone (P<0.01), indicating a synergistic effect of 5-FU and PAN-811 on suppression of growth of human lung cancer cell H460. In membrane integrity analysis (FIG. 5(f)), 25 µM 5-FU resulted in a 124% increase in LDH reading in the culture supernatant, while 10 µM PAN-811 led to a 30% increase in the LDH reading. A cotreatment with 100 µM 5-FU and 10 µM PAN-811 enhanced LDH reading by 40%, which is much lower than that in the group with 25 µM 5-FU alone. It indicates an inhibitory effect of PAN-811 on 5-FU-caused membrane leakage. A 3-day treatment with 3.5 µM CDDP, 10 µM PAN-811, or both greatly decreased the cell density of H460 in culture. Quantitatively, 3.5 µM CDDP and 10 µM PAN-811 reduced MTS readings by 22% and 75%, respectively (FIG. 5(d)). A cotreatment with 3.5 µM CDDP and 10 µM PAN-811 reduced MTS readings by 85%, which shows a statistically significant difference from CDDP (P<0.01 by ANOVA) or PAN-811 alone (P<0.01 by t-test), indicating a synergistic effect of CDDP and PAN-811 on suppression of growth of human lung cancer cell H460. In membrane integrity analysis (FIG. 5(g)), 3.5 µM CDDP resulted in a 71% increase in LDH reading in the culture supernatant, while 10 µM PAN-811 led to a 30% increase in the LDH reading. A cotreatment with 3.5 µM CDDP and 10 µM PAN-811 enhanced LDH reading by 57%, which is a statistically significant difference from that in the group with 3.5 µM CDDP alone (P<0.01), demonstrating an inhibitory effect of PAN-811 on CDDP-induced membrane leakage. In general, PAN-811 did not show any inhibition in the effect of MTX, 5-FU, or CDDP on cell growth of H460 cells, although it manifested an inhibitory effect on MTX-, 5-FU-, or CDDP-induced membrane leakage. A synergistic effect between 5-FU and PAN-811 or between CDDP and PAN-811 occurred on suppression of H460 cell survival.

While the invention has been described with reference to certain exemplary embodiments thereof, those skilled in the art may make various modifications to the described embodiments of the invention without departing from the scope of the invention. The terms and descriptions used herein are set forth by way of illustration only and not meant as limitations. In particular, although the present invention has been described by way of examples, a variety of compositions and processes would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A method for the treatment of chemotherapy induced peripheral neuropathy comprising the step of administering to a patient in need thereof a composition comprising a neuroprotective compound of 3-aminopyridine-2-carboxaldehyde thiosemicarbazone (PAN-811), wherein PAN-811 is the only active ingredient.

2. The method of claim 1, wherein the step of administering is intravenous, intraperitoneal, subcutaneous, intramuscular, topical, transdermal or oral.

3. The method of claim 1, wherein the composition is an injectable and/or infusible solution.

4. The method of claim 1, wherein the composition is formulated as a micro emulsion.

5. The method of claim 1, wherein the composition is formulated as a liposome.

6. A method for the treatment of chemotherapy-induced peripheral neuropathy comprising administering to a patient a neuroprotective composition comprising at least one thiosemicarbazone compound of Formula I, or an analogue thereof:

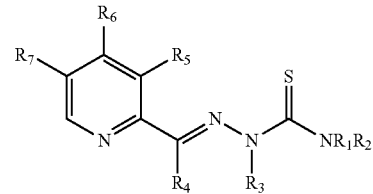

wherein the thiosemicarbazone compound is the only active ingredient.

7. The method of claim 6, wherein the at least one thiosemicarbazone compound comprises the compound of Formula II, or an analogue thereof:

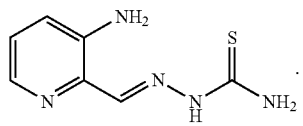 [SMILES: NC(=S)N/N=C/c1ncccc1N]

8. The method of claim 6, wherein the step of administering is intravenous, intraperitoneal, subcutaneous, intramuscular, topical, transdermal or oral.

9. The method of claim 6, wherein the composition is an is an injectable and/or infusible solution.

10. The method of claim 6, wherein the composition is formulated as a micro emulsion.

11. The method of claim 6, wherein the composition is formulated as a liposome.

12. A method for the treatment of chemotherapy induced peripheral neuropathy comprising of the step of administering to a patient a composition comprising a thiosemicarbazone, wherein the thiosemicarbazone is the only active ingredient.

* * * * *